(12) United States Patent
Yoon et al.

US008815795B2

(10) Patent No.: US 8,815,795 B2
(45) Date of Patent: Aug. 26, 2014

(54) METHODS FOR PREVENTING OR TREATING EYE DISEASES USING ADIPONECTIN

(71) Applicant: Industry Foundation of Chonnam National University, Gwangju (KR)

(72) Inventors: Kyung Chul Yoon, Gwangju (KR); Je Moon Woo, Ulsan (KR); Hun Taeg Chung, Ulsan (KR)

(73) Assignee: Industry Foundation of Chonnam National University, Gwangju (KR)

( * ) Notice: Subject to any disclaimer, the term of this patent is extended or adjusted under 35 U.S.C. 154(b) by 0 days.

(21) Appl. No.: 13/684,641

(22) Filed: Nov. 26, 2012

(65) Prior Publication Data

US 2014/0037712 A1    Feb. 6, 2014

(30) Foreign Application Priority Data

Aug. 2, 2012  (KR) .................. 10-2012-0084864

(51) Int. Cl.
*A61K 38/00*    (2006.01)
*A61K 38/22*    (2006.01)
*C07K 14/575*   (2006.01)
*A61P 29/00*    (2006.01)
*A61K 9/127*    (2006.01)

(52) U.S. Cl.
CPC .............. *A61K 38/22* (2013.01); *A61K 9/127* (2013.01); *A61K 38/2264* (2013.01)
USPC ............. 514/1.1; 514/9.7; 514/12.2; 454/450

(58) Field of Classification Search
CPC ........ A61K 38/17; A61K 38/22; A61K 9/127
See application file for complete search history.

(56) References Cited

U.S. PATENT DOCUMENTS

2003/0224425 A1*  12/2003  Blondel et al. ................ 435/6.16
2006/0035824 A1*   2/2006  Lodish et al. .................. 514/9.4
2008/0221030 A1*   9/2008  Bora et al. ..................... 514/6.9

OTHER PUBLICATIONS

Shichi et al. "Cataract Formation and Prevention", 2004, Expert Opin. Investig. Drugs, vol. 13. pp. 691-701.*
Klein R., Age-related eye disease, visual impairment, and driving in the elderly, Hum Factors. Oct. 1991;33(5):521-5.*
Berg et al, ACRP30/adiponectin: an adipokine regulating glucose and lipid metabolism,TRENDS in Endocrinology & Metabolism vol. 13 No. 2 Mar. 2002.*
Ralph, Conjunctival goblet cell density in normal subjects and in dry eye syndromes, Invest Ophthalmol Apr. 1975;14(4):299-302.*
Albietz et al, The conjunctival epithelium in dry eye subtypes: effect of preserved and non-preserved topical treatments, Curr Eye Res, Jan. 2001;22(1):8-18.*
Kyung Chul Yoon, Han Jin Oh, Zhengri Li, Ji-Suk Choi, Je Moon Woo, Effectiveness of Topical Adiponectin in a Mouse Model of Experimental Dry Eye, 284 Dry Eye Disease II, Program No. 2338, Poster Board No. A355, ARVO 2012 Annual Meeting Abstracts, May 7, 2012.
Morihiro Matsuda et al., Rittenhouse, Role of Adiponectin in Preventing Vascular Stenosis, The Journal of Biological Chemistry, vol. 277, No. 40, Issue of Oct. 4, pp. 37487-37491, 2002.
Noriyuki Ouchi et al., Novel Modulator for Endothelial Adhesion Molecules—Adipocyte-Derived Plasma Protein Adiponectin, Circulation, Dec. 21/28, 1999.
Anna M. Wolf et al., Adiponectin induces the anti-inflammatory cytokines IL-10 and IL-1RA in human leukocytes, Biochemical and Biophysical Research Communications 323 (2004) 630-635.

* cited by examiner

*Primary Examiner* — Marcela M Cordero Garcia
*Assistant Examiner* — Sergio Coffa
(74) *Attorney, Agent, or Firm* — The PL Law Group, PLLC

(57) ABSTRACT

A composition for preventing or treating an eye disease includes adiponectin as an active ingredient. Adiponectin as an active ingredient is eventually revealed to show prevention or therapeutic efficacies for eye diseases such as dry eye (syndrome), inflammatory eye disease and side effects due to the use of contact lenses by promoting tear secretion, alleviating ocular surface irregularities, decreasing inflammatory cytokines on the ocular surface and lacrimal gland, and increasing conjunctival goblet cell density. In addition, the composition having eye contact lubrication effects may be used as cleaners or lubricants for preventing non-bacterial inflammation due to wearing contact lenses.

11 Claims, 10 Drawing Sheets

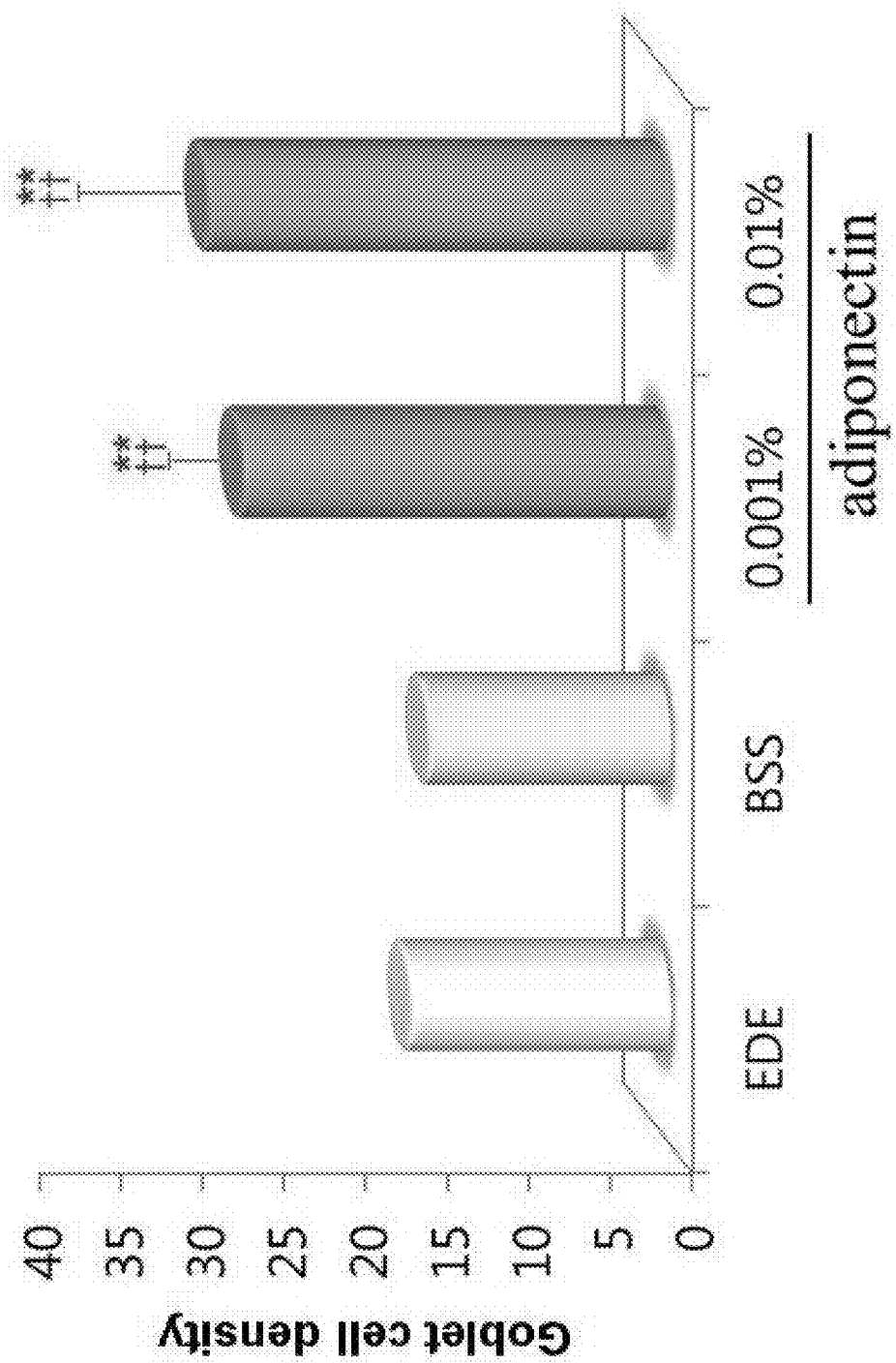

SEQUENCE LISTING

```
<160> NUMBER OF SEQ ID NOS: 2

<210> SEQ ID NO 1
<211> LENGTH: 247
<212> TYPE: PRT
<213> ORGANISM: Adipocyte complement-related protein Acrp30

<400> SEQUENCE: 1

Met Leu Leu Leu Gln Ala Leu Leu Phe Leu Leu Ile Leu Pro Ser His
 1               5                   10                  15

Ala Glu Asp Asp Val Thr Thr Thr Glu Glu Leu Ala Pro Ala Leu Val
             20                  25                  30

Pro Pro Pro Lys Gly Thr Cys Ala Gly Trp Met Ala Gly Ile Pro Gly
         35                  40                  45

His Pro Gly His Asn Gly Thr Pro Gly Arg Asp Gly Arg Asp Gly Thr
     50                  55                  60

Pro Gly Glu Lys Gly Glu Lys Gly Asp Ala Gly Leu Leu Gly Pro Lys
 65                  70                  75                  80

Gly Glu Thr Gly Asp Val Gly Met Thr Gly Ala Glu Gly Pro Arg Gly
                 85                  90                  95

Phe Pro Gly Thr Pro Gly Arg Lys Gly Glu Pro Gly Glu Ala Ala Tyr
            100                 105                 110

Met Tyr Arg Ser Ala Phe Ser Val Gly Leu Glu Thr Arg Val Thr Val
        115                 120                 125

Pro Asn Val Pro Ile Arg Phe Thr Lys Ile Phe Tyr Asn Gln Gln Asn
    130                 135                 140

His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
                165                 170                 175

Ser Leu Phe Lys Lys Asp Lys Ala Val Leu Phe Thr Tyr Asp Gln Tyr
            180                 185                 190

Gln Glu Lys Asn Val Asp Gln Ala Ser Gly Ser Val Leu Leu His Leu
        195                 200                 205

Glu Val Gly Asp Gln Val Trp Leu Gln Val Tyr Gly Asp Gly Asp His
    210                 215                 220

Asn Gly Leu Tyr Ala Asp Asn Val Asn Asp Ser Thr Phe Thr Gly Phe
225                 230                 235                 240

Leu Leu Tyr His Asp Thr Asn
                245

<210> SEQ ID NO 2
```

<211> LENGTH: 1276
<212> TYPE: DNA
<213> ORGANISM: Adipocyte complement-related protein Acrp30 mRNA, complete cds

<400> SEQUENCE: 2

```
ctctaaagat tgtcagtgga tctgacgaca ccaaaagggc tcaggatgct actgttgcaa      60
gctctcctgt tcctcttaat cctgcccagt catgccgaag atgacgttac tacaactgaa     120
gagctagctc ctgctttggt ccctccaccc aagggaactt gtgcaggttg gatggcaggc     180
atcccaggac atcctggcca caatggcaca ccaggccgtg atggcagaga tggcactcct     240
ggagagaagg gagagaaagg agatgcaggt cttcttggtc ctaagggtga gacaggagat     300
gttggaatga caggagctga agggccacgg ggcttccccg gaaccoctgg caggaaagga     360 gagcctggag aagccgctta tatgtatcgc tcagcgttca gtgtggggct ggagacccgc     420
gtcactgttc ccaatgtacc cattcgcttt actaagatct tctacaacca acagaatcat     480
tatgacggca gcactggcaa gttctactgc aacattccgg gactctacta cttctcttac     540
cacatcacgg tgtacatgaa agatgtgaag gtgagcctct tcaagaagga caaggccgtt     600
ctcttcacct acgaccagta tcaggaaaag aatgtggacc aggcctctgg ctctgtgctc     660
ctccatctgg aggtgggaga ccaagtctgg ctccaggtgt atggggatgg ggaccacaat     720
ggactctatg cagataacgt caacgactct acatttactg gctttcttct ctaccatgat     780
accaactgac tgcaactacc catagcccat acaccaggag aatcatggaa cagtcgacac     840
actttcagct tagtttgaga gattgatttt attgcttagt ttgagagtcc tgagtattat     900
ccacacgtgt actcacttgt tcattaaacg actttataaa aaataatttg tgttcctagt     960
ccagaaaaaa aggcactccc tggtctccac gactcttaca tggtagcaat aacagaatga    1020
aaatcacatt tggtatgggg gcttcacaat attcgcatga ctgtctggaa gtagaccatg    1080 ctattttttct gctcactgta cacaaatatt gttcacataa accctataat gtaaatatga    1140
aatacagtga ttactcttct cacaggctga gtgtatgaat gtctaaagac ccataagtat    1200
taaagtggta gggataaatt ggaaaaaaaa aaaaaaaaaa agaaaaactt tagagcacac    1260
tggcggccgt tactag                                                   1276
```

METHODS FOR PREVENTING OR TREATING EYE DISEASES USING ADIPONECTIN

CROSS-REFERENCE TO RELATED APPLICATIONS

This application claims priority from Korean Patent Application No. 2012-0084864, filed on Aug. 2, 2012, in the Korean Intellectual Property Office, the disclosure of which is incorporated herein by reference.

BACKGROUND

1. Field of the Invention a. The present invention relates to methods for preventing or treating an eye disease using adiponectin.

2. Description of the Related Art

Dry eye (dry eye syndrome) is a common disease which is occurred in 20% of Korean adults. It is known as a disease which can damage to the ocular surface by inducing ocular uncomfortable feeling, decreased visual acuity and instability of tear film caused by tears and inflammation of ocular surface (cornea and conjunctiva) rather than simple lack of tears. This disease is believed to have features such as ocular pain, corneal surface irregularity, blurred and fluctuating vision and increased risk of corneal ulcer; however, the pathogenesis of dry eye disease has not been clearly established. However, there are increasing studies to support that inflammation plays an important role in dry eye disease characterized by inflammatory cell infiltration, increased expression of immune activation molecules and adhesion molecules, Th1 and Th17 responses, apoptosis markers and chemokine[1-5].

Adiponectin is a hormone protein secreted mainly by the adipose tissue[6] and has many pleiotropic effects such as protective adipocytokine in obesity-related metabolic and cardiovascular disorders[7-9]. It is associated to attenuation of insulin resistance, atherosclerosis and cardiac remodeling. Accumulating evidence suggests that adiponectin also exert a potent immunoregulatory effect, as evidenced by increased levels of anti-inflammatory cytokines interleukin (IL)-10 and IL-1 receptor antagonist (IL-1RA) and decreased levels of pro-inflammatory IL-6, TNF-α, and interferon (IFN)-γ[10-12].

Adiponectin was shown to reduce the phagocytic activity of macrophages and inhibit the production of chemokines and chemokine receptors. It is known to have effects on anti-diabetic, anti-atherosclerosis, of anti-tumor formation and anti-inflammatory by inhibiting inflammatory cytokines such as TNF-α (tumor necrosis factor-alpha), interleukin-6 and interferon-γ (interferon-gamma)[14]. In addition, the anti-inflammatory effect of adiponectin in chronic inflammatory diseases such as uveitis, and rheumatoid arthritis[13] has been reported in several clinical and experiment studies[15]. It is now accepted that adiponectin can have anti-inflammatory effects[16-17]. Although there is considerable evidence of the roles of adiponectin in the pathogenesis of many chronic inflammatory diseases such as rheumatoid arthritis, very little is known about roles of adiponectin in dry eye disease. To date, studies evaluating the efficacy of the topical application of adiponectin have not been performed.

Throughout this application, several patents and publications are referenced and citations are provided in parentheses. The disclosures of these patents and publications are incorporated herein by reference in order to more fully describe this invention and the state of the art to which this invention pertains.

SUMMARY

The present inventors have made intensive studies to develop substance preventing or treating for an eye disease. As a result, they have found out that adiponectin is significantly effective in improvements or treatments of an eye disease by promoting tear production, alleviating ocular surface irregularities, decreasing inflammatory cytokines on the ocular surface and lacrimal gland, and increasing conjunctival goblet cell density in a mouse model of experimental dry eye.

Accordingly, it is an aspect of this invention to provide a composition for preventing or treating an eye disease.

It is another aspect of this invention to provide an artificial tear composition.

It is still another aspect of this invention to provide a composition for cleaning, lubricating or packaging a contact lens.

It is a further aspect of this invention to provide a method for preventing or treating an eye disease.

It is a further aspect of this invention to provide a method for lubricating or moisturizing an eye.

It is a further aspect of this invention to provide a method for cleaning or lubricating a contact lens.

In one aspect of the present invention, there is provided a composition for preventing or treating an eye disease including a protein including the amino acid sequence as set forth in SEQ ID NO:1 as an active ingredient.

In another aspect of the present invention, there is provided a pharmaceutical composition for preventing or treating eye diseases including (a) a therapeutically effective amount of a protein including the amino acid sequence as set forth in SEQ ID NO:1; and (b) a pharmaceutically acceptable carrier.

In still another aspect of the present invention, there is provided an artificial tear composition including a protein including the amino acid sequence as set forth in SEQ ID NO:1 as an active ingredient.

In further aspect of the present invention, there is provided a composition for cleaning, lubricating or packaging a contact lens, including a protein including the amino acid sequence as set forth in SEQ ID NO:1 as an active ingredient.

In still further aspect of the present invention, there is provided a method for preventing or treating an eye disease, including administrating to a subject in need thereof a therapeutically effective amount of a composition including a protein including the amino acid sequence as set forth in SEQ ID NO:1 as an active ingredient.

In further aspect of the present invention, there is provided a method for lubricating or moisturizing an eye, including applying topically to an eye of a subject in need thereof an artificial tear composition including a protein including the amino acid sequence as set forth in SEQ ID NO:1 as an active ingredient.

In still further aspect of the present invention, there is provided a method for cleaning or lubricating a contact lens, including contacting to the contact lens a composition including a protein including the amino acid sequence as set forth in SEQ ID NO:1 as an active ingredient.

Other aspects and advantages of the present invention will become apparent from the detailed description to follow taken in conjugation with the appended claims and drawings.

BRIEF DESCRIPTION OF THE DRAWINGS

FIG. 3a shows mean goblet cell densities and FIG. 3b shows representative figures stained with periodic acid-Schiff (PAS) reagent in the experimental dry eye (EDE) control, balanced salt solution (BSS)-treated, 0.001% adiponectin-treated, and 0.01% adiponectin-treated groups at day 10 post EDE induction. †P<0.05, ††P<0.01 compared with the BSS group. Scale bar=20 nm.

DETAILED DESCRIPTION OF THIS INVENTION

Figure 1:
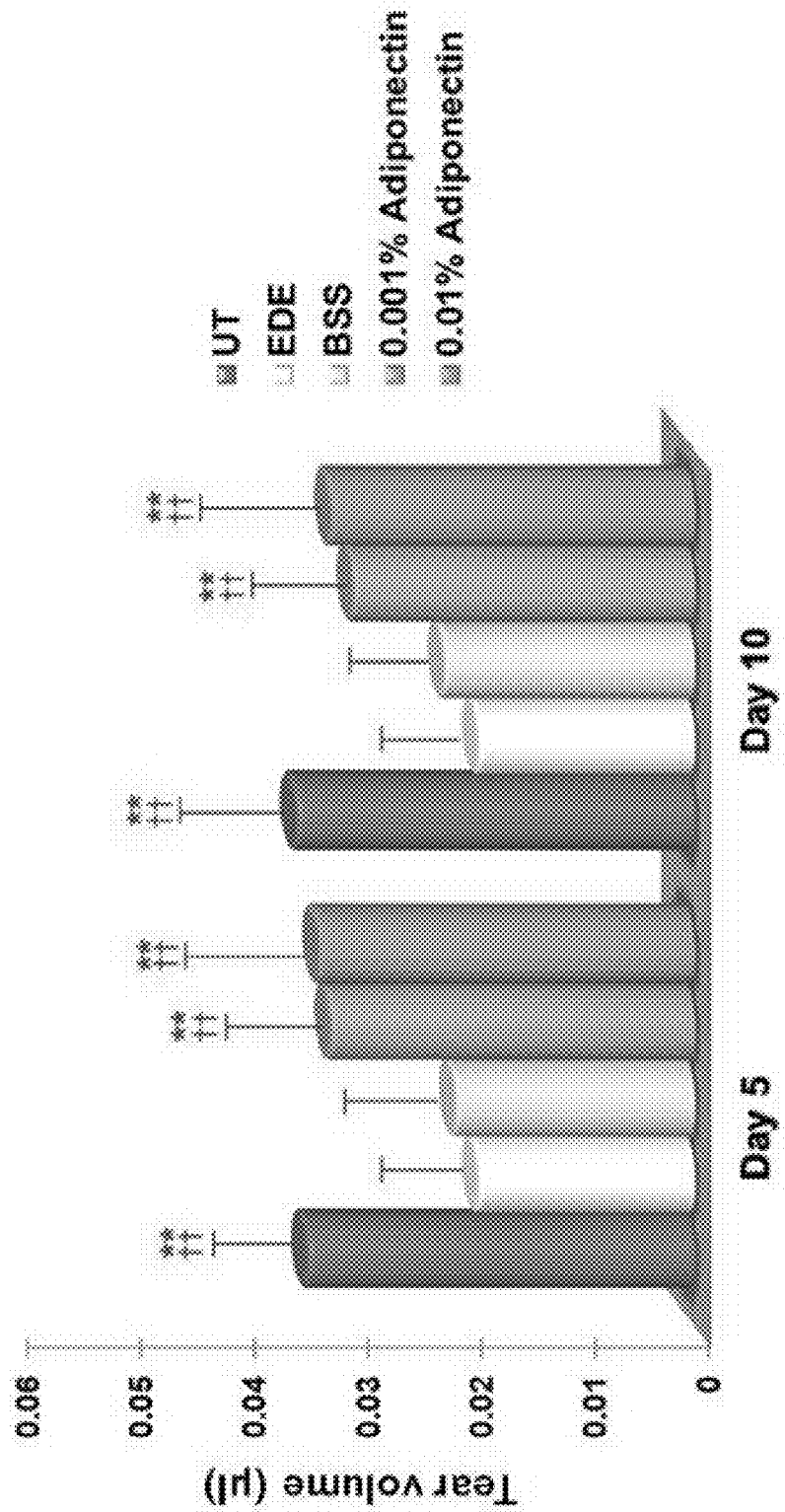
FIG. 1 shows mean tear volumes in the experimental dry eye (EDE) control, balanced salt solution (BSS)-treated, 0.001% adiponectin-treated, and 0.01% adiponectin-treated groups at day 5 and 10 post EDE induction. *P<0.05, **P<0.01 compared with the EDE group. †P<0.05, ††P<0.01 compared with the BSS group.

The present inventors have made intensive studies to develop substance preventing or treating for an eye disease. As a result, it has been found out that adiponectin is significantly effective in improvements or treatments of an eye disease by promoting tear production, alleviating ocular surface irregularities, decreasing inflammatory cytokines on the ocular surface and lacrimal gland, and increasing conjunctival goblet cell density in a mouse model of experimental dry eye.

In one aspect of the present invention, there is provided a composition for preventing or treating an eye disease including a protein including the amino acid sequence as set forth in SEQ ID NO:1 as an active ingredient.

Adiponectin as an active ingredient used in one or more embodiments of the present invention is eventually revealed to show prevention or therapeutic efficacies for eye diseases such as dry eye (syndrome), inflammatory eye disease and side effects due to the use of contact lenses by promoting tear secretion, alleviating ocular surface irregularities, decreasing concentrations of IL-1β, IL-6, TNF-α, IFN-γ and MIG and percentages of CD4$^+$ CXCR3$^+$ T cells in the conjunctiva, and increasing conjunctival goblet cell density.

According to an embodiment, the eye diseases are dry eye (syndrome), inflammatory eye diseases or side effects due to the use of contact lenses.

According to an embodiment, the inflammatory eye diseases are selected from the group consisting of infectious eye diseases, allergic eye disease, keratitis, conjunctivitis, uveitis, meibomian gland dysfunction, Stevens-Johnson syndrome and Sjöegren syndrome.

According to an embodiment, the side effects due to the use of contact lenses are ocular uncomfortable feeling, dryness, burning sensation, stinging feeling or non-bacterial inflammation.

The composition of an embodiment of the present invention may be administered orally or parenterally. When the composition of an embodiment of the present disclosure is administered parenterally, the pharmaceutical composition of an embodiment of the present disclosure may be administered with an intravenous injection, a subcutaneous injection, an intramuscular injection, an intraperitoneal injection, percutaneous administration, mucosal administration and eye drop administration. For example, it may be administered with mucosal administration and eye drop administration.

The composition of an embodiment of the present invention may decrease the inflammatory cytokine.

For example, the inflammatory cytokine in the present invention may be IL-1, IL-2, IL-3, IL-4, IL-5, IL-6, IL-7, IL-8, IL-9, IL-10, IL-11, IL-12, IL-13, TNF-α, TNF-β, TGF-β (transforming growth factor-β), MIG (CXCL9) or interferons (IFNs), preferably IL-1, IL-6, TNF-α, interferons or MIG, more preferably IL-1β, IL-6, TNF-α, IFN-γ or MIG.

As proven in the following examples, where adiponectin of the present invention is treated in a mouse model of experimental dry eye, the levels of inflammatory cytokines such as IL-1β, IL-6, TNF-α, IFN-γ and MIG is significantly decreased. These decreases of inflammatory cytokines inhibit inflammatory responses, resulting in prevention or treatment for inflammatory diseases.

The composition of an embodiment of the present invention may increase the number of conjunctival goblet cell. Tears have three components of outer oily layer, middle watery layer and inner mucus layer. When at least one component among them is lacked, a tear film is unstable and dry eye can occur. The inner mucus layer is mucous component secreted from goblet cells in the conjunctiva and thinly covers cornea and conjunctiva. It makes that the tear film is fixed on the surface of the eye. As proven in the following examples, where adiponectin of the present invention is administered with topical administration, density of conjunctival goblet cell increased and finally it leads to promote tear production.

The composition of an embodiment of the present invention may decrease corneal surface irregularity. The corneal surface irregularity may be occurred by corneal diseases, damages or surgeries. As proven in the following examples, adiponectin of the present invention decreases corneal surface irregularity caused by dry eye and inflammatory diseases.

In another aspect of the present invention, there is provided a pharmaceutical composition for preventing or treating eye diseases including (a) a therapeutically effective amount of a protein including the amino acid sequence as set forth in SEQ ID NO:1; and (b) a pharmaceutically acceptable carrier.

The term used herein "a therapeutically effective amount" means sufficient quantity to achieve efficacies or activities of a protein including the amino acid sequence as set forth in SEQ ID NO:1 as mentioned above.

When the composition of an embodiment of the present disclosure is prepared as a pharmaceutical composition, the pharmaceutical composition of the present disclosure may include a pharmaceutically acceptable carrier. The pharmaceutically acceptable carrier included in the pharmaceutical composition of the present disclosure may be one commonly used in the preparation of formulations and includes lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable excipients and formulations are described in detail in *Remington's Pharmaceutical Sciences* (19th ed., 1995), which is incorporated herein by reference.

The pharmaceutical composition of an embodiment of the present disclosure may be administered orally or parenterally. When the composition of an embodiment of the present disclosure is administered parenterally, the pharmaceutical composition of the present disclosure may be administered with an intravenous injection, a subcutaneous injection, an intramuscular injection, an intraperitoneal injection, percutaneous administration, mucosal administration and eye drop administration. For example, it may be administered with mucosal administration and eye drop administration.

An appropriate administration dosage of the pharmaceutical composition of the present disclosure may be determined variously depending on such factors as a preparation method, an administration method, an age, a body weight and a gender of a patient, a pathological condition, a diet, an administration time, an administration route, an excretion rate or a response sensitivity. For example, a daily dosage of adult of the pharmaceutical composition of the present disclosure may be 0.001-100 mg/kg (weight), particularly 0.01-80 mg/kg (weight), more particularly 0.1-60 mg/kg (weight). In addition, the doses may be administered once or several times a day in accordance with judgments of doctors or pharmacists. Specially, in the case of eye drop administration, the doses may be dropped once or several times a day to eye in the ranges from 0.001% to 3% (w/v, the same as above), for example, from 0.01% to 1%.

The pharmaceutical composition of an embodiment of the present disclosure may be prepared into a unit dosage form or multiple dosage form along with a pharmaceutically acceptable carrier and/or excipient according to a method that can be easily employed by those skilled in the art.

According to an embodiment, the formulation of the composition of an embodiment of the present invention may be solution, suspension, syrup, emulsion, extract, dust, powder, granule, tablet, sustained-release, eye drop, capsule, contact lens cleaner or contact lens lubricant and may further include a dispersant or stabilizer.

Specifically, according to administration routes, solid preparations for oral administration may include capsule, tablet, pill, powder and granule.

In these solid preparations, active compounds may be mixed with one or more pharmaceutically acceptable excipient or carrier (for example, sodium citrate or dicalcium phosphate) and/or a) filler or extender (for example, starch, lactose, sucrose, glucose, mannitol, and silicic acid), b) binder (for example, carboxymethyl cellulose, alginate, gelatin, polyvinylpyrrolidone, sucrose and gum arabic), c) humectant (for example, glycerol), d) disintegrating agent (for example, agar-agar, calcium carbonate, potato or tapioca starch, alginic acid, certain silicates, and sodium carbonate), e) liquid type retarder (for example, paraffin), f) absorption accelerators (for example, quaternary ammonium compound), g) wetting agents (for example, cetylalcohol and glycerol monostearate), h) absorbents (for example, kaolin and bentonite clay), i) lubricants (for example, talc, calcium stearate, magnesium stearate, solid polyethylene glycol, sodium lauryl sulfate, and mixtures thereof), and a combination thereof. The formulations of capsule, tablet and pill may also include buffer.

In addition, high molecular weight polyethylene glycol as well as excipients such as lactose or milk sugar may used as a filler for soft and hard gelatin capsules.

Solid administration forms such as tablet, sugarcoated pill, capsule, pill and granule may be prepared using a shell and a coating such as enteric coatings and other well-known coatings. These may optionally include an opacification agent. Also, these may be prepared to allow releasing only an active ingredient or releasing an active ingredient in a sustained manner or preferential manner in specific portions of intestinal canal. Active ingredients may be formulated into a microcapsule together with at least one excipient mentioned above, if necessary.

Specially, for eye drop administration, the composition of an embodiment of the present invention may be prepared by mixing with required ingredients commonly used in pharmaceutics such as purified water, an isotonic agent (for example, sodium chloride, glycerin), surfactant (for example, polysorbate 80, polyoxyethylene alkyl ether), preservative (for example, edetate sodium, sorbate sodium), buffer (for example, sodium phosphate) and pH adjusting agent (for example, hydrochloric acid, sodium hydroxide). For example, the pH is adjusted around neutral pH (pH 5 to 8) and the osmotic pressure is adjusted around 1.

Liquid preparations for oral administration include pharmaceutically acceptable emulsion, solution, suspension, syrup and elixirs. Besides active compounds, liquid preparations may include inactivity diluents commonly used in the art, such as water or various solvent, solubilizing agent and emulsifier (for example, ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn oil, germ oil, olive oil, castor oil and sesame oil), glycerol, tetrahydrofurfuryl alcohol, polyethylene glycol, and sorbitan fatty acid ester and mixtures thereof). The oral composition also may include an adjuvant such as a wetting agent, an emulsifier, a suspending agent, a sweetening agent, a flavor and a fragrance, in addition to inactive diluents.

An appropriate formulation for an embodiment of the parenteral injection may include physiologically acceptable sterile aqueous or non-aqueous solution, dispersion, suspension or emulsion, and sterile injectable solution or sterile powder for reconstitutable dispersion. For examples of an appropriate aqueous and non-aqueous carrier, diluent, solvent or vehicle include water, ethanol, polyol (propylene glycol, polyethylene glycol, glycerol), vegetable oil (olive oil), injectable organic ester (for example, ethyl oleate) and appropriate mixtures thereof.

In addition, the composition of the present invention may include adjuvants such as preservative, wetting agent, emulsifier and dispersing agent. Various antibacterial and antifungal agents (for example, paraben, chlorobutanol, phenol, sorbate) may inhibit the action of microorganisms. Also, preferably, osmotic stabilizers such as sugars and sodium chloride may be included. The absorption of the injectable pharmaceutical drugs may be delayed using an absorption retarder (for example, aluminum monostearate and gelatin).

A suspension may include suspending agent (for example, ethoxylated isostearyl alcohol, polyoxyethylene sorbitol and sorbitan ester, microcrystalline cellulose, aluminum metahydroxide, bentonite, agar-agar and tragacanth or mixtures thereof) in addition to the active compounds.

For maintaining efficacies of drugs, the pharmaceutical composition may be administered by a subcutaneous injection or an intramuscular injection such that the drug may be gradually absorbed, which may be achieved using liquid suspension of low water-soluble crystalline or non-crystalline materials. The absorption rate of the drug is dependent on the dissolution rate, and the dissolution rate is dependent on the size and form of crystals. In the meantime, delayed absorption of parenterally administered drug may be achieved by dissolving or suspending drugs in an oil vehicle.

A depot form for injection may be provided as microcapsule matrix using biodegradable polymers such as polylactide-polyglycolide. The release rates of the drug may be controlled by depending on the ratios of the drug versus the polymer and characteristics of particular polymer used. Examples of other biodegradable polymer include poly (orthoester) and poly(anhydride). In addition, the depot form for injection may be prepared by capturing drugs in biocompatible liposomes or microemulsions.

An injectable formulation may be sterilized, for example, by bacterial-retention filter or a sterilization agent.

When the composition of the present disclosure is prepared as a formulation for parenteral administration, the formulation is liposome, sustained-release or eye drop.

The stability of the pharmaceutical composition of the present invention may be improved by encapsulating into liposome.

The liposome used in an embodiment of the present invention may be prepared by mixtures including polyol, surfactants, phospholipids, fatty acids and water (Prescott, Ed. *Methods in Cell Biology*, (XIV), p. 33et seq. (1976), which is incorporated herein by reference).

The Polyol used in the liposome is not particularly limited, for example, propylene glycol, dipropylene glycol, 1,3-butylene glycol, glycerin, methylpropanediol, isoprene glycol, pentyleneglycol, erythritol, xylitol, and sorbitol, most preferably propylene glycol.

The surfactant used in preparation of the liposome may include anything known to one of skill in the art, for example, anionic surfactant, cationic surfactant, ampholytic surfactant and nonionic surfactant. For example, anionic surfactant and nonionic surfactant may be used. Specific examples of the anionic surfactant include alkylacylglutamate, alkylphosphates, alkyllactylate, dialkylphosphate and trialkylphosphate, but are not limited thereto. Specific examples of the nonionic surfactant include alkoxylatedalkylether, alkoxylatedalkylester, alkylpolyglycoside, polyglycerylester and sugar ester, but are not limited thereto. For example, polysorbate may be used.

Another ingredient, a phospholipid, used in preparation of liposome is used as biphilic lipid and may include natural phospholipid (e.g., lecithin from egg yolk or lecithin from soybean, sphingomyelin) and synthetic phospholipid (e.g. dipalmitoylphosphatidylcholine or hydrogenated lecithin), for example, lecithin. More particularly, the lecithin may be unsaturated or saturated lecithin extracted from egg yolk or from soybean. In lecithin derived from natural products, the amount of phosphatidyl choline is usually 23-95%, and the amount of phosphatidylethanolamine is usually less than 20%.

The fatty acid used in preparation of the liposome as higher fatty acid may include lauric acid, myristic acid, palmitic acid, stearic acid, oleic acid and linoleic acid as C12-22 alkyl chain saturated or unsaturated fatty acids, but not limited thereto. Water used in preparation of the liposome is commonly deionized water, but not limited thereto.

Preparations of the liposome may be achieved through various methods known in the art, for example, by applying the mixture containing the above ingredients to high pressure homogenizer.

The prepared liposome system has some advantages to enhance drug delivery efficiency by dissolving many types of sparingly soluble material and stabilizing unstable materials.

The pharmaceutical composition of an embodiment of the present invention may be prepared in a sustained-release formulation for maintaining the effective blood concentration of the active ingredient, thereby reducing the drug administration frequency to enhance patient compliance is improved.

The sustained-release formulation is prepared by including sustained-release carrier and other supplements in addition to the active ingredient of the present invention. The sustained-release carrier used in the present invention may be used various methods known in the art, for example, polyethyleneoxide.

In addition, a diluted carrier commonly used in the pharmaceutics may be included as other supplements. Examples of the diluted carrier used for this purpose include lactose, dextrin, starch, microcrystalline cellulose, dibasic calcium phosphate, calcium carbonate, sugars and silicon dioxide. Besides, in order to increase the liquidity, a slip modifier such as zinc stearate or magnesium stearate, or other supplements available in the pharmaceutics may be included.

In still another aspect of the present invention, there is provided an artificial tear composition which includes a protein including the amino acid sequence as set forth in SEQ ID NO:1 as an active ingredient.

Since the protein including the amino acid sequence as set forth in SEQ ID NO:1 used as an active ingredient in an embodiment of the present invention is the same with the active ingredient used in the composition for preventing or treating an eye disease of the present invention of the described above, the common descriptions between them are omitted in order to avoid undue redundancy leading to the complexity of this specification.

According to an embodiment, the active ingredient used in the artificial tear composition of the present invention promotes tear secretion in lacrimal gland to show prevention or therapeutic efficacies for dry eye (syndrome).

The artificial tear composition in an embodiment of the present invention may further include electrolyte, nonionic surfactant, antimicrobial, borate and polyol complex or low molecular weight amino acid.

The electrolyte included in the artificial tear composition is used to stimulate natural tear, and it includes ion contained in natural tears. For example, the electrolyte used in the present invention may be potassium, calcium, magnesium and zinc, and the concentration have been described in U.S. Pat. No. 5,403,598, which is incorporated herein by reference.

The nonionic surfactant used in the composition of an embodiment of the present invention decrease surface tension of the composition of the present invention so that the solution is spread on the corneal surface evenly. The nonionic surfactant includes various surfactants known in the art, for example polysorbates such as polysorbate 80 (Tween 80) having hydrophilic-lipophilic balance (HLB) value of more than 15, and a block copolymer of ethylene oxide and propylene oxide. The amount of surfactant used in the composition of the present invention means a sufficient amount to provide the composition having approximately 38 to 45 dynes/cm of the surface tension, and the surface tension of the range mentioned-above correspond to the surface tension of the natural tears.

The artificial tear composition of an embodiment of the present invention may be prepared to single-dose or multi-dose product. The single-dose product requires no antimicrobial preservative to maintain aseptic conditions after manufacturing but multi-dose product may require it.

The antimicrobial preservative used in the composition of an embodiment of the present invention includes, for example, polyquaternium-1 and the content is from 0.1 to 10 ppm. In order to improve the antimicrobial activity of antimicrobial preservatives in the composition of the present invention further includes borate/polyol complex or low molecular weight amino acids.

The content of the borate/polyol complex is from 0.5% to 6.0% by weight based on the total weight of the composition, preferably from 1.0% to 2.5% by weight.

The molar ratio of borate and polyol is from 1:0.1 to 1:10, for example, from 1:0.25 to 1:2.5. The borate used in the present invention refers to boric acid, salts of boric acid, other pharmaceutically acceptable borate or combinations thereof, preferably boric acid, sodium borate, potassium borate, calcium borate, magnesium borate or combinations thereof.

The polyol includes various polyol known in the art, for example, sugar, sugar alcohol, and sugar acid, particularly, mannitol, sorbitol, propylene glycol and glycerol, more particularly, glycerol.

Contents of the low molecular weight amino acid used in the compositions of an embodiment of the present invention in order to improve the antimicrobial activity is from 0.01 to 2.5 w/v %, particularly from 0.1 to 1.0 w/v %, the molecular weight is, for example, from 75 to 250 and, for example, glycine.

The artificial tear composition of an embodiment of the present invention may be prepared to have pH and osmotic pressure compatible with eye. For example, the pH is from 6.8 to 7.8 and the osmotic pressure is from 250 to 350 mOsm/kg.

When the composition of an embodiment of the present disclosure is applied to an eye for increasing a comfort and a residence time of the composition, the artificial tear composition of the present disclosure is prepared to have improved viscosity. For example, the viscosity is from 1 to 20 cps, from 2 to 20 cps, or from 5 to 20 cps.

The artificial tear composition of an embodiment of the present invention may be applied topically on cornea to prevention or treatment a dry eye and used as an eye wetting agent or a lubricant by dropping the one or two drops on the cornea.

In further aspect of the present invention, there is provided a composition for cleaning, lubricating or packaging a contact lens, including a protein including the amino acid sequence as set forth in SEQ ID NO:1 as an active ingredient.

The contact lens cleaning composition of an embodiment of the present invention may include a surfactant as a main ingredient and the protein including the amino acid sequence as set forth in SEQ ID NO:1 as an auxiliary ingredient. The surfactant having cleaning action may include various surfactants known in the art, including anionic, cationic, nonionic, and amphoteric surfactant as a main cleaner. The representative anionic surfactant includes sulfated surfactants, sulfonated surfactants and physiologically acceptable salts thereof which are provided an excellent cleaning activity to lipid, protein and sediments of contact lens. The example includes sodium lauryl sulfate, sodium laureth sulfate (sodium salt of sulfated and ethoxylated lauryl alcohol), ammonium laureth sulfate (ammonium salt of sulfated and ethoxylated lauryl alcohol), sodium trideceth sulfate (sodium salt of sulfated and ethoxylated tridecyl alcohol), sodium dodecyl benzene sulfonate, 2sodium lauryl or laureth sulfosuccinate (lauryl sulfonate succinic acid lauryl or ethoxylated lauryl alcohol ½ disodium salt of ester), 2sodium oleamido sulfosuccinate, and dioctyl sodium sulfosuccinate (2-ethylhexyl alcohol and sodium salt of diester of sulfonate succinic acid).

The nonionic surfactant having an excellent cleaning activity includes certain polyoxyethylene, polyoxypropylene block copolymers (poloxamer) surfactant, including various commercial surfactants such as brand name Pluronic (for example, Pluronic P104 or L64) from BASF Corporation.

The composition of an embodiment of the present invention may include a cationic surfactant, and the representative cationic surfactant is triquaternary phosphate ester. In addition, the composition of the present invention may include a amphoteric surfactant, and the representative amphoteric surfactant is imidazoline derivatives and N-alkyl amino acids.

In the contact lens lubricating composition of an embodiment of the present invention, the protein including the amino acid sequence as set forth in SEQ ID NO:1 promotes tear secretion in lacrimal gland as mentioned-above, whereby secreted tear forms tear film on surface of contact lens to act lubrication. Therefore, the protein including the amino acid sequence as set forth in SEQ ID NO:1 may be used, especially as an active ingredient in lubricating compositions.

The contact lens packaging composition of the present invention is an aqueous solution used for contact lens storage, and commonly includes brine, and other buffer solution and deionized water but is not limited thereto. For example, the packaging composition of the present invention is a salt-containing brine including sodium chloride, sodium borate, sodium phosphate, dibasic sodium phosphate, monobasic sodium phosphate or potassium salt of correspond to thereof. These ingredients are likely to form buffer solutions including acid and its conjugate base. The buffer solution further includes 2-(N-morpholino)ethanesulfonic acid (MES), sodium hydroxide, 2,2-bis(hydroxymethyl)-2,2',2"-nitriletriethanol, n-tris(hydroxymethyl)methyl-2-ethanesulfonic acid, citric acid, sodium citrate, sodium carbonate, sodium bicarbonate, acetic acid, sodium acetate and mixtures thereof.

The features and advantages of one or more embodiments of the present invention will be summarized as follows:

(a) The present invention provides a composition for preventing or treating eye diseases including adiponectin as an active ingredient.

(b) Adiponectin as an active ingredient used in the present invention is eventually revealed to show prevention or therapeutic efficacies for eye diseases such as dry eye (syndrome), inflammatory eye disease and side effects due to the use of contact lenses by promoting tear secretion, alleviating ocular surface irregularities, decreasing inflammatory cytokines on the ocular surface and lacrimal gland, and increasing conjunctival goblet cell density.

(c) The compositions of the present invention having eye contact lubrication effects may be used as cleaners or lubricants for preventing non-bacterial inflammation due to wearing contact lenses.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods
Mouse Model of Thy Eye and Experimental Procedure
This research protocol was approved by the Chonnam National University Medical School Research Institutional Animal Care and Use Committee. Maintenance of animals and all in vivo experiments were performed in accordance with institutional guidelines and the ARVO Statement for the Use of Animals in Ophthalmic and Vision Research.

Six to eight-week-old female C57BL/6 mice was used in these experiments. EDE was induced by subcutaneous injection of 0.5 mg/0.2 mL scopolamine hydrobromide (Sigma-Aldrich, St. Louis, Mo.) four times a day (8 am, 11 am, 2 pm and 5 pm) with exposure to an air draft and 30% ambient humidity for 18 hours per day. During these experiments, the animal's behaviors, food, and water intake were not restricted. The mice were divided into five groups according to the topical treatment administered as follows: untreated (UT) controls; EDE controls (received no eyedrops); EDE and balanced salt solution (BSS; Alcon, Forth Worth, Tex.); EDE and 0.001% adiponectin; or EDE and 0.01% adiponectin. Adiponectin eyedrops were made by dilution gAdiponectin/gAcro30 solution (R&D systems, Minneapolis, Minn.) with BSS. All treatment groups received 2 µL of eyedrops four times a day. Tear volume and corneal smoothness were measured at 5 and 10 days post EDE induction. Ten days after initiation of EDE, the mice were euthanized, and multiplex immunobead assay, histology, immunohistochemistry, and flow cytometry were performed. Each group comprised of 10 animals (for a total of twenty eyes), and all experiments were repeated.

Measurement of Tear Production

Tear volume was measured using phenol-red impregnated cotton threads (Zone-Quick, Oasis, Glendora, Calif.) as previously described. Briefly, the threads were held with jewelers forceps and placed in the lateral canthus for 20 seconds. The tear volume, expressed in millimeters of thread wet by the tear and turned red, was read using a microscope (SMZ 1500; Nikon, Melville, N.Y.). A standard curve was derived to convert distance into volume.

Evaluation of Corneal Smoothness

Reflected images of a white ring from the fiber-optic ring illuminator of the stereoscopic zoom microscope (SMZ 1500; Nikon) were taken immediately after enthanasia. Corneal smoothness was assessed by grading the distortion of the white ring reflected off the corneal epithelium in digital images by two masked observers. The corneal irregularity severity score was calculated using a 5 point scale (0-5) based on the number of distorted quarters in the reflected ring: 0, no distortion; 1, distortion in one quarter of the ring; 2, distortion in two quarters; 3, distortion in three quarters; 4, distortion in all four quadrant; 5, severe distortion, in which no ring could be recognized.

Multiplex Immunobead Assay

The levels of IL-1β, IL-6, TNF-α, IFN-γ, and MIG in the conjunctiva and lacrimal gland were measured using a multiplex immunobead assay (Luminex 200; Luminex Corp., Austin, Tex.). Conjunctival and lacrimal gland tissues were collected from each group and pooled in lysis buffer containing protease inhibitors for 30 minutes. The cell extracts were centrifuged, and the supernatants were stored at −70° C. until use. The supernatants were added to wells containing the appropriate cytokine bead mixture that included mouse monoclonal antibodies specific for IL-1β, IL-6, TNF-α, IFN-γ MIG, or (Panomics, Santa Clara, Calif.) for 60 minutes. A standard curve was generated by adding serial dilutions of cytokines to wells. The plate was incubated for 30 minutes at room temperature with the biotinylated detection antibody. After three washes with assay buffer, the reactions were detected by addition of streptavidin-phycoerythrin using an analysis system (xPONENT, Austin, Tex.).

Histology

Eye and lacrimal gland were surgically excised, fixed in 4% paraformaldehyde, and embedded in paraffin. Six-micrometer sections were stained with periodic acid-Schiff (PAS) reagent. Sections from 4 mice of each group were examined and photographed with a microscope (Olympus, Tokyo, Japan) equipped with a digital camera. Goblet cell density in the superior and inferior conjunctiva was measured in 3 sections from each eye using image-analysis software (Media Cybernetics, Silver Spring, Md.) and expressed as the number of goblet cells per 100 p.m.

Immunohistochemistry

Immunohistochemistry was performed to detect and count cells that stained positively for TNF-α in the conjunctiva and lacrimal glands. Eyes and lacrimal glands were surgically excised and, immersed in 4% paraformaldehyde overnight at 4° C. The tissue blocks were washed, dehydrated, embedded in paraffin, cut at to a thickness of 3 µm, and mounted. After fixation, endogenous peroxidases were quenched with 0.3% $H_2O_2$ in PBS for 10 minutes. Non-specific staining in the sections was inhibited by sequential blocking using avidin/biotin block (Vector Laboratories, Burlingame, Calif.) for 10 minutes. Following this, sections were blocked with 20% normal serum in phosphate buffered saline (PBS) for 45 minutes, followed by incubation with a monoclonal goat anti-TNF-α antibody (Santa Cruz, Heidelberg, Germany) for 1 hour at room temperature. After the sections were washed, they were incubated with biotinylated mouse anti-goat secondary antibody. The samples were then incubated with 3,3'-diaminobenzidine peroxidase substrate (NovaRed; Vector Laboratories, Burlingame, Calif.) and counterstained with Mayer's hematoxylin.

Flow Cytometry

Flow cytometry was performed to count the number of $CD4^+$ $CXCR3^+$ T cells from the conjunctiva and lacrimal gland as previously described, with modifications. Conjunctival and lacrimal gland tissues from each group were harvested and dipped in PBS. The tissues were teased apart with scissors and shaken at 37° C. for 60 minutes in the presence of 0.5 mg/mL collagenase type D (Roche Applied Science, Indianapolis, Ind.). Following incubation, the tissues were disrupted by grinding with a syringe plunger and passed through a cell strainer with a pore size of 100-micrometer. Cells were centrifuged at 1500 rpm for 7 minutes and resuspended in PBS with 1% bovine serum albumin. Cells were washed and counted by trypan blue staining. The samples were incubated with fluorescein-conjugated anti-CD4 antibody (BD Biosciences, San Jose, Calif.), phycoerythrin-conjugated anti-CXCR3 antibody (BD Biosciences), and isotype control antibody at 37° C. for 30 minutes. Flow cytometry was performed using a FACSCalibur cytometer with CellQuest software (BD Biosciences).

Statistical Analysis

Results are presented as the mean±SEM. The statistical significance of differences among the groups was determined by using the one-way analysis of variance (ANOVA) test with Tukey post hoc analysis and the Mann-Whitney U test using SPSS 17.0 software (SPSS Inc., Chicago, Ill., USA). A P value less than 0.05 was considered statistically significant.

Results

Aqueous Tear Production

The mean tear volume in the EDE group was significantly decreased at 5 days (P<0.01) post EDE induction compared with UT. The mean tear volumes 5 days post EDE induction were 0.02±0.02 µL in the BSS-treated group (P=0.41 compared with the EDE control), 0.03±0.01 µL in the 0.001% adiponectin-treated group (P<0.05 compared with the EDE control or BSS-treated groups), and 0.03±0.02 µL in the 0.01% adiponectin-treated group (P<0.05 compared with the EDE control or BSS-treated groups). The tear volumes in 0.001% adiponectin-treated group and 0.01% adiponectin-treated group were significantly increased both of at 5 days and 10 days compared with the EDE control and BSS-treated groups. The mean volumes in all groups at 10 days post EDE induction were similar to those at 5 days (FIG. 1).

Changes of Corneal Surface Irregularities

Figure 2A:
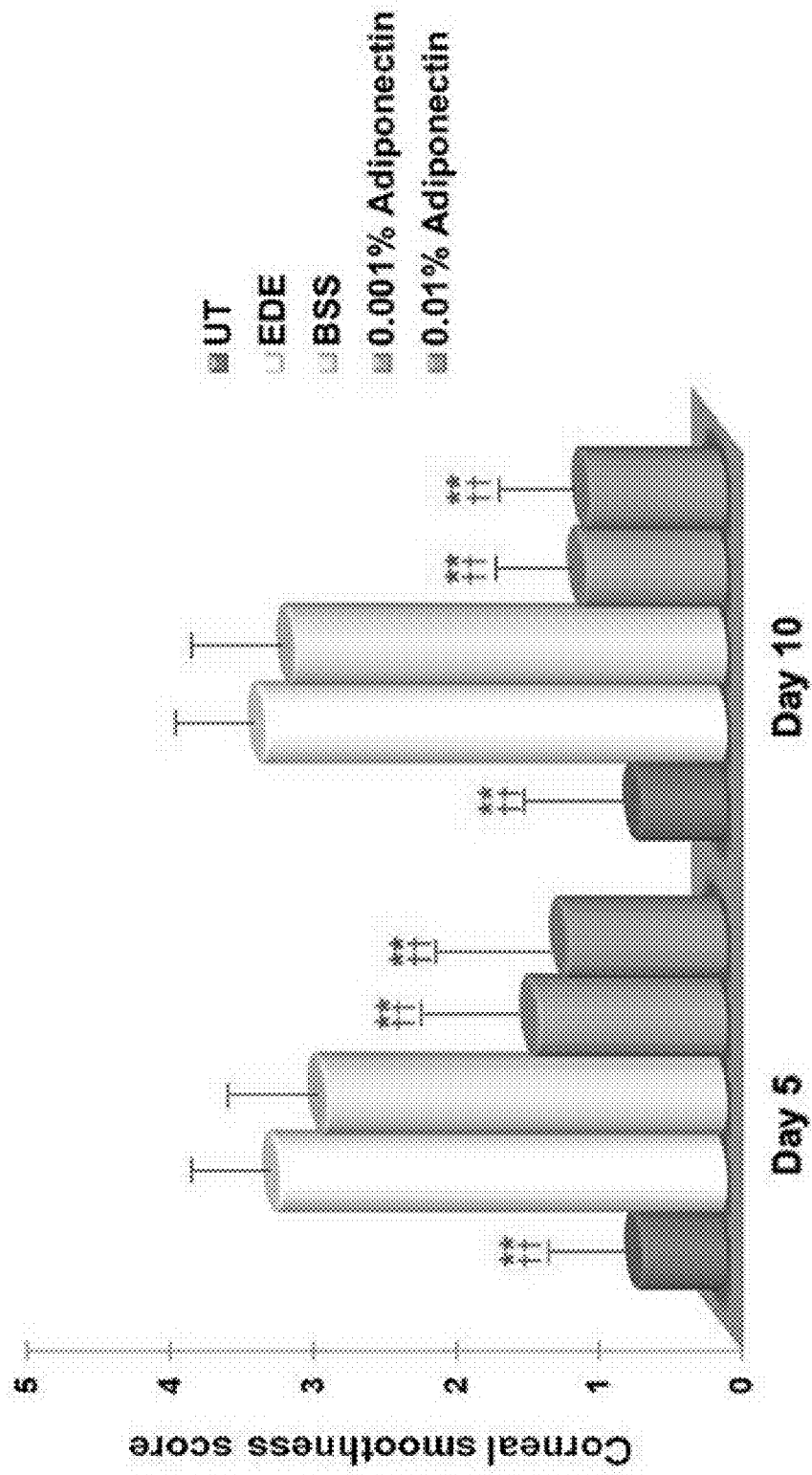
FIG. 2a shows mean corneal smoothness scores and FIG. 2b shows representative figures in the experimental dry eye (EDE), balanced salt solution (BSS)-treated, 0.001% adiponectin-treated, 0.01% adiponectin-treated at day 5 and 10 post EDE induction. *P<0.05, **P<0.01 compared with the EDE group. †P<0.05, ††P<0.01 compared with the BSS group.
Figure 2B:
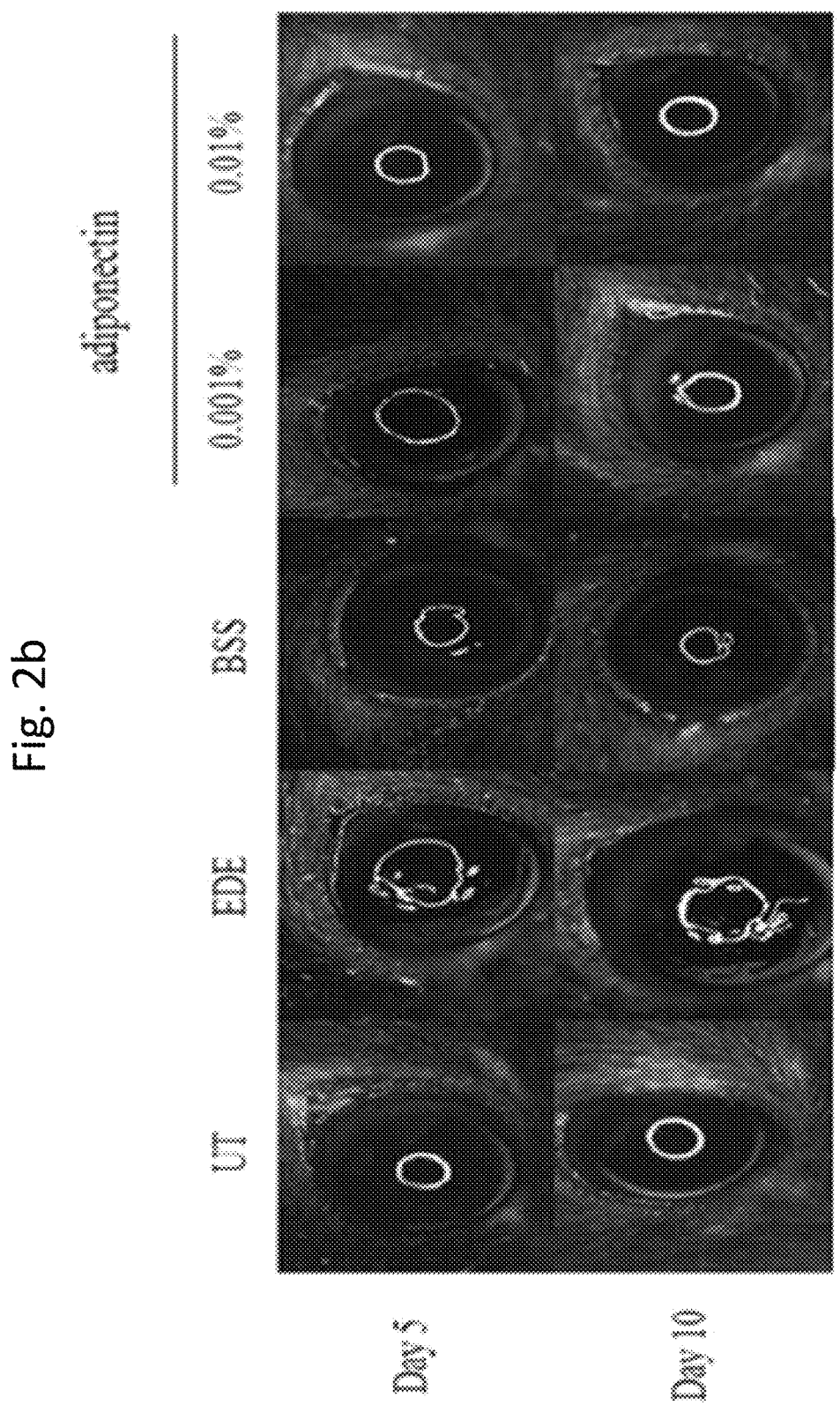

The mean corneal smoothness score in the EDE group was significantly decreased at 5 days (P<0.01) post EDE induction compared with UT. The mean corneal smoothness scores 5 days post EDE induction were 2.68±0.80 in the BSS-treated group (P=0.63 compared with the EDE control), 1.21±0.62 in the 0.001% adiponectin-treated group (P<0.05 compared with the EDE control or BSS-treated groups), and 1.10±0.53 in the 0.01% adiponectin treated group (P<0.05 compared with the EDE control or BSS-treated groups). The corneal smoothness score in 0.001% adiponectin-treated group and 0.01% adiponectin-treated group were significantly improved both at 5 days and 10 days compared with the EDE control and BSS-treated groups. The mean scores in all groups at 10 days post EDE induction were similar to those at 5 days (FIGS. 2A-B).

Inflammatory Cytokine Levels in Conjunctival Tissues and Lacrimal Gland

Figure 3B:
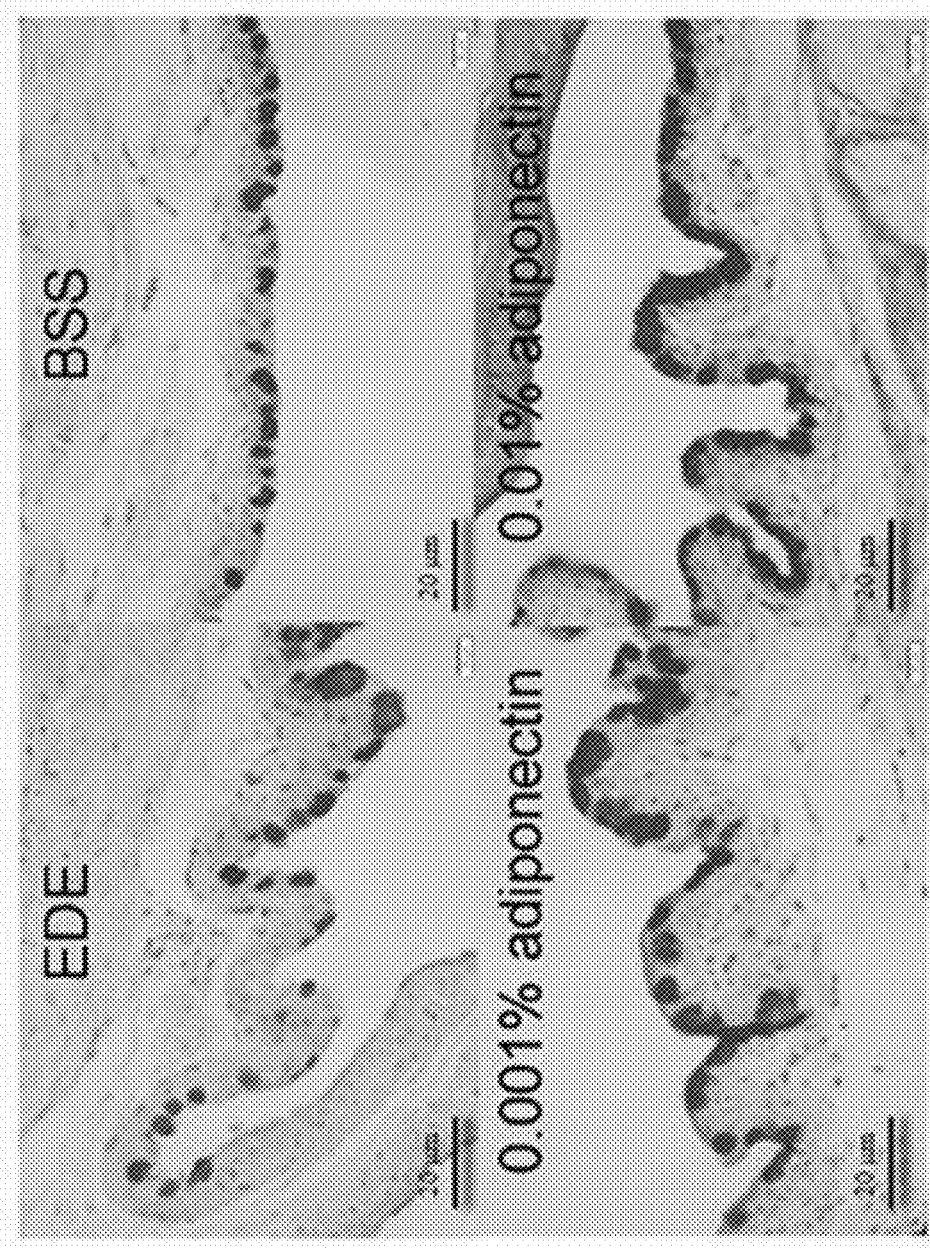
Figure 4:
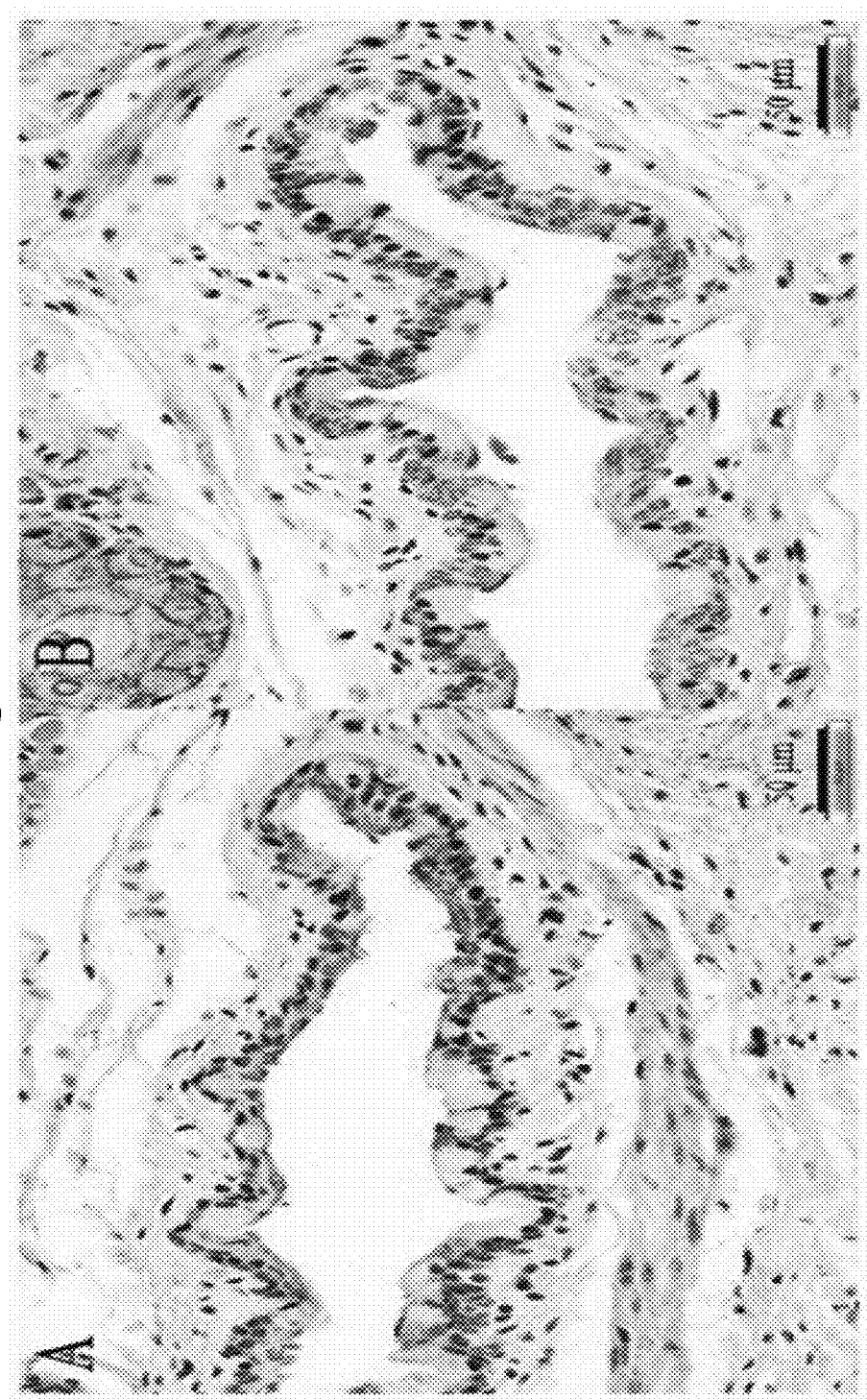
FIG. 4 represents immunohistochemistry showing the expression of adiponectin receptors, AdipoR1 (A) and AdipoR2 (B), in the conjunctiva of normal untreated mice. Scale bar=50 μm.

The concentrations of IL-1β, IL-6, TNF-α, IFN-γ and MIG in the conjunctiva and lacrimal gland significantly increased 10 days after the induction of EDE (P<0.05). Conjunctival and lacrimal gland IL-1β, IL-6, TNF-α, IFN-γ and MIG concentrations in the BSS-treated groups were not significantly different when compared with EDE control group (Table 1-2). However, the 0.001% and 0.01% adiponectin-treated groups showed significantly lower levels of IL-1β, IL-6, TNF-α, IFN-γ and MIG compared with those in the EDE control or BSS-treated groups (P<0.05).

adiponectin-treated groups were significantly higher compared with those in the EDE control or BSS-treated group (P<0.05) (FIGS. 3A-B).

TNF-α Expression in Conjunctival Tissues and Lacrimal Gland

Figure 5A:
FIGS. 5a and 5b represent immunohistochemistry for TNF-α in the conjunctiva (FIG. 5a) and lacrimal gland (FIG. 5b) from experimental dry eye (EDE) control, balanced salt solution (BSS)-treated, 0.001% adiponectin-treated, and 0.01% adiponectin-treated mice. TNF-α was visualized by 3,3'-diaminobenzidine peroxidase staining (brown stain). Sections were counterstained with Mayer's hematoxylin (blue stain). Scale bars=50 μm (conjunctiva), 200 nm (lacrimal gland).
Figure 5B:
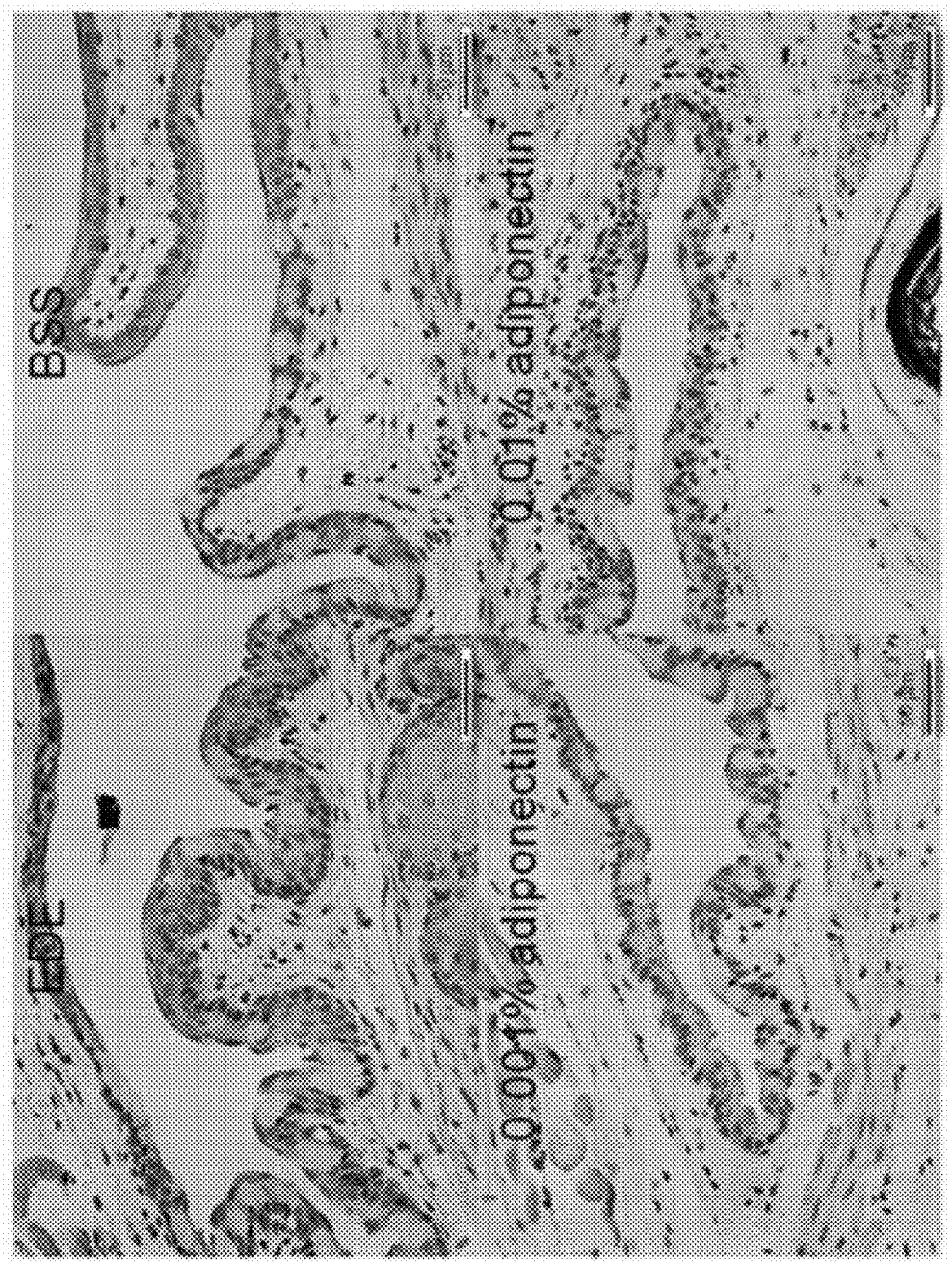

Immunohistochemical staining for TNF-α in the conjunctival epithelium and lacrimal gland increased after the induction of EDE, but remained unchanged in mice treated with BSS. However, conjunctival and lacrimal gland TNF-α staining decreased in mice treated with 0.001% and 0.01% adiponectin solutions (FIGS. 5A-B).

Flow Cytometric Analysis

The mean percentages of CD4$^+$ CXCR3$^+$ T cells in the conjunctival and lacrimal gland were significantly increased 10 days post-induction of EDE (P<0.05). The mean percentages of CD4$^+$ CXCR3$^+$ T cells in the conjunctiva were 58.91±20.21% in the EDE group, 57.29±19.37% in the BSS group (P=0.68 compared with EDE group), 32.51±12.45% in the 0.001% adiponectin group (P<0.05 compared with the EDE or BSS group), and 30.71±12.55% in the 0.01% adiponectin group (P<0.05 compared with the EDE or BSS group). The mean percentages of CD4$^+$ CXCR3$^+$ T cells in the lacrimal gland were 67.51±24.6% in the EDE group, 62.46±21.30% in the BSS group (P=0.32 compared with EDE group), 39.26±13.60% in the 0.001% adiponectin

TABLE 1

The concentrations of IL-1β, IL-6, TNF-α, IFN-γ and MIG in the conjunctiva

|   | IL/1β (pg/ml) | IL-6 (pg/ml) | TNF-α (pg/ml) | IFN-γ (pg/ml) | MIG (μg/ml) |
|---|---|---|---|---|---|
| UT | 1.19 ± 0.51**†† | 0.87 ± 0.23**† | 0.52 ± 0.28**†† | 21.87 ± 4.02**†† | 1.96 ± 0.61**†† |
| EDE | 6.25 ± 1.15 | 2.87 ± 0.98 | 1.34 ± 0.58 | 45.56 ± 8.77 | 4.53 ± 0.89 |
| BSS | 7.30 ± 2.21 | 1.99 ± 0.23 | 1.07 ± 0.48 | 42.87 ± 5.98 | 4.87 ± 1.01 |
| 0.001% adiponectin | 1.25 ± 0.56**†† | 1.13 ± 0.56**†† | 0.55 ± 0.34**†† | 30.78 ± 5.07*† | 2.87 ± 0.56*† |
| 0.01% adiponectin | 1.22 ± 0.60**†† | 0.97 ± 0.43**†† | 0.57 ± 0.33**†† | 31.36 ± 4.98*† | 2.27 ± 0.53*† |

UT: untreated group
*P < 0.05,
**P < 0.01 compared with the EDE group.
†P < 0.05,
††P < 0.01 compared with the BSS group.

TABLE 1

The concentrations of IL-1β, IL-6, TNF-α, IFN-γ and MIG in the lacrimal gland

|   | IL/1β (pg/ml) | IL-6 (pg/ml) | TNF-α (pg/ml) | IFN-γ (pg/ml) | MIG (μg/ml) |
|---|---|---|---|---|---|
| UT | 22.57 ± 5.39**†† | 30.54 ± 8.10**†† | 0.61 ± 0.41**†† | 83.78 ± 14.21*† | 40.06 ± 10.21**†† |
| EDE | 46.52 ± 7.19 | 69.15 ± 10.89 | 3.24 ± 0.97 | 145.72 ± 28.95 | 86.91 ± 19.26 |
| BSS | 42.21 ± 6.99 | 55.46 ± 14.87 | 3.01 ± 1.05 | 110.49 ± 25.33 | 65.82 ± 11.50 |
| 0.001% adiponectin | 32.33 ± 7.13*† | 35.53 ± 8.66**†† | 0.85 ± 0.30**†† | 93.12 ± 15.24*† | 48.10 ± 16.36**†† |
| 0.01% adiponectin | 31.22 ± 7.20*† | 33.17 ± 7.67**†† | 0.80 ± 0.32**†† | 89.36 ± 14.68*† | 42.08 ± 17.23**†† |

UT: untreated group
*P < 0.05,
**P < 0.01 compared with the EDE group.
†P < 0.05,
††P < 0.01 compared with the BSS group.

Conjunctival Goblet Cell Density

The mean density of conjunctival goblet cells was significantly decreased 10 days post-induction of EDE. The mean goblet cell density in the BSS-treated groups was not significantly different compared with the EDE control group, whereas the mean cell densities in the 0.001% and 0.01% (P<0.05 compared with the EDE or BSS group), and 30.35±11.87%, in the 0.01% adiponectin groups (P<0.05 compared with the EDE or BSS group).

Figure 6A:
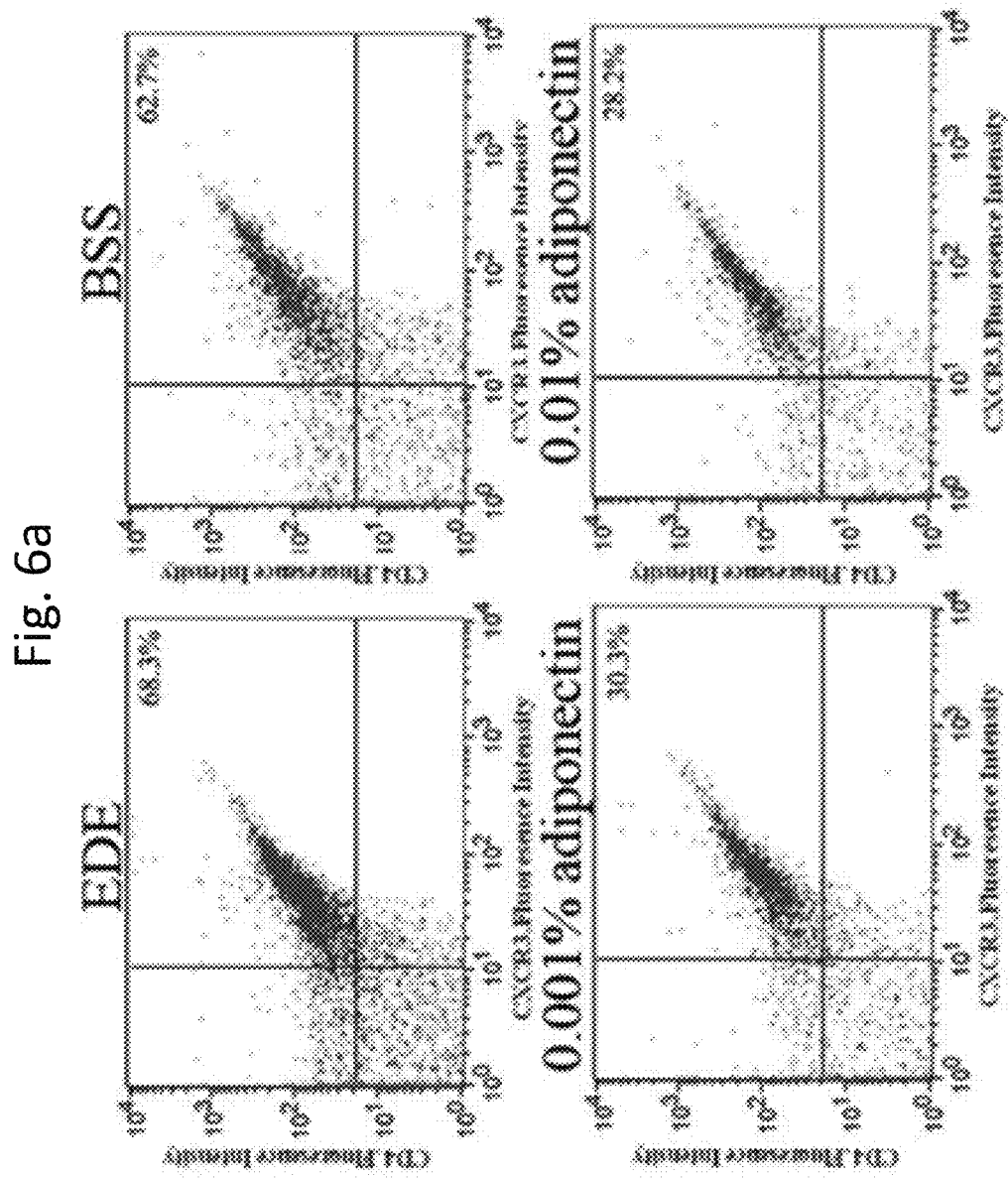
FIGS. 6a and 6b represents Flow cytometry showing CD4$^+$ CXCR3$^+$ T cells in the conjunctiva (FIG. 6a) and lacrimal gland (FIG. 6b) from experimental dry eye (EDE) control, balanced salt solution (BSS)-treated, 0.001% adiponectin-treated, and 0.01% adiponectin-treated mice.
Figure 6B:
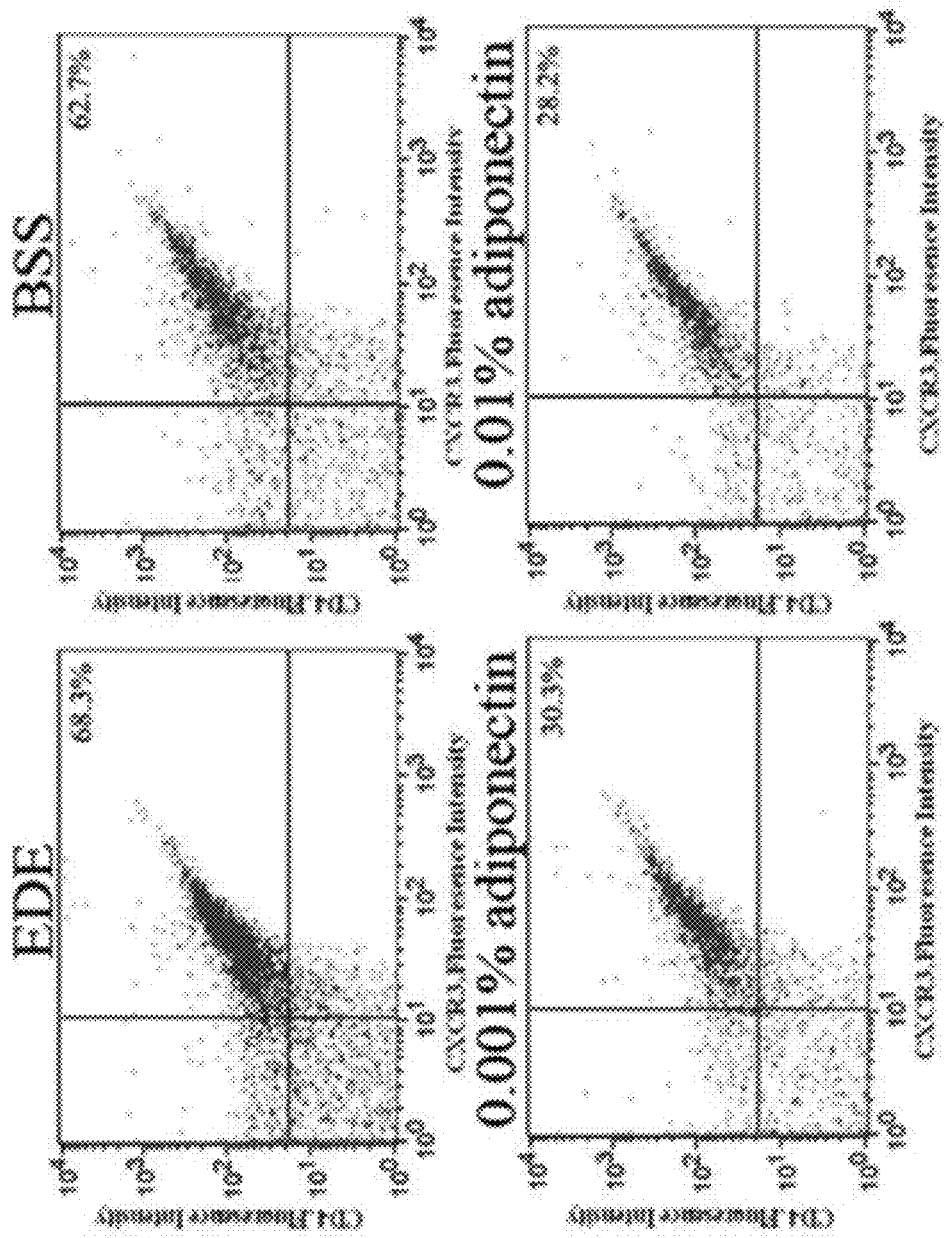

The number of CD4$^+$ CXCR3$^+$ T cells in 0.001% adiponectin-treated group and 0.01% adiponectin-treated group were decreased compared with other groups. Histograms of percentages of CD4+ CXCR3+ T cells from representative samples in the EDE, BSS, 0.001%, and 0.01% adiponectin-treated groups are shown in FIG. 6A-B.

The identification of adiponectin receptors include Adiponectin receptor 1 AdipoR1, adiponectin receptor 2 (AdipoR2), and T-cadherin. And it widely distributed in peiphetal tissues and organs. Recent studies demonstrated adiponectin receptors also distributed in the rat eyes. AdipoR1 has a high affinity for globular adiponectin and a low affinity for full-length adiponectin, whereas AdipoR2 has an intermediate affinity for full-length and globular adiponectin. T-cadherin is a truncated receptor that can bind the hexameric and high molecular weight oligomeric forms of adiponectin. AdipoR1 and AdipoR2 interact with the adaptor protein containing a pleckstrin homology domain, a phosphotyrosine domain and a leucine zipper motif (APPL1), which binds the N-terminal intracellular domains of the receptors. The binding of adiponectin to its receptors provokes the activation of adenosine monophosphate (AMP)-activated protein kinase (AMPK), and the activation of various signaling molecules such as p38 mitogen-activated protein kinase (p38 MAPK). Activation of AMPK can also block the nuclear factor κB (NFκB) signaling, known to be a mediator of inflammation in endothelial cells.

Adiponectin in inflammatory processes was recently reported in clinical cases of rheumatoid arthritis (RA), a disorder in which infiltrating leukocytes create a constant inflammatory state leading to premature joint degradation. Serum and synovial fluid adiponectin levels are significantly higher in patients with this form of arthritis than in healthy or osteoarthritis patients. In addition, the serum adiponectin concentration correlates with the degree of severity of RA. Adiponectin AdipoR1 and AdipoR2 mRNA and protein are present in rheumatoid synovial fibroblasts (RSF), suggesting a paracrine action of adiponectin in joints. It should be noted that the treatment of synovial fibroblasts with adiponectin induces the production of IL-6 and pro-matrix metalloproteinase-1 (pro-MMP-1), the precursor of the matrix-degrading enzyme MMP-1, through the p38 MAPK pathway. Adiponectin can also inhibit the development of acute viral myocarditis, through an increase in AdipoR1 immunoreactivity, and attenuates angiotensin-II-induced cardiac hypertrophy.

The inventors of the present invention evaluated the effect of adiponectin eyedrops on tear production, ocular surface irregularities, inflammatory cytokines in the conjunctiva and lacrimal gland, conjunctival goblet cell density, and conjunctival CD4+ CXCR3+ T cells in an experimentally induced mouse dry eye model. Tear volumes at 5 and 10 days and conjunctival goblet cell densities at 10 days post EDE induction were higher in the 0.001% and 0.01% adiponectin-treated groups compared with the EDE control and BSS-treated groups. Corneal smoothness scores at 5 and 10 days and IL-1β, IL-6, TNF-α, and MIG concentrations in conjunctival tissues and lacrimal gland, TNF-α in the conjunctival epithelium or lacrimal gland, and percentages of CD4+ CXCR3+ T cells in the conjunctiva and lacrimal gland at 10 days post EDE induction were lower in the 0.001% and 0.01% adiponectin-treated groups compared with the EDE control and BSS-treated groups. There was no statistically significant difference in the parameters between the BSS-treated and EDE control group. The present invention showed an improvement in the clinical and histological parameters after treatment with 0.001%, and 0.01% adiponectin solutions in mice with EDE. Compared with previous studies evaluating the efficacy of adiponectin, our animal study had several different features. First, the inventors induced experimental dry eye in the C57BL/6 mouse strain which is not susceptible to spontaneous autoimmunity, compared with autoimmune-susceptible strains such as the non-obese diabetic (NOD) mouse which develops spontaneous dry eye and SS-like inflammation. The inventors previously reported that EDE can be reversed after the elimination of desiccating stress in the C57BL/6 mouse, whereas it remained unchanged in the autoimmune NOD mouse. Further studies are required to evaluate the effect of topical infliximab to treat SS using autoimmune mouse models.

The inventors report the first use of the topical application of adiponectin eyedrops in the treatment of experimental dry eye. Adiponectin therapy has anti-inflammatory effects which can enhance T cell receptor-mediated Th1 cell and chemokine activation in peripheral blood and prevent the migration of pathogenic T cells to inflamed tissues, thereby inhibiting inflammation in target tissues. Topical adiponectin can affect the inflamed ocular surface directly. Considering these features, the topical administration of adiponectin may be more beneficial in the treatment of ocular surface inflammation such as dry eye. Further clinical studies on the efficacy of topical adiponectin in patients with dry eye disease are required. In conclusion, the application of 0.01%, and 0.1% adiponectin eyedrops can improve tear production and ocular surface irregularities, decrease inflammatory cytokines and Th1 cells on the ocular surface, and increase conjunctival goblet cell density in mouse experimental dry eye. The present invention suggests that adiponectin as TNF-α blocking agent may be useful for the treatment of dry eye disease.

Having described exemplary embodiments of the present invention, it is to be understood that variants and modifications thereof falling within the spirit of the invention may become apparent to those skilled in this art, and the scope of this invention is to be determined by appended claims and their equivalents.

REFERENCES

1. Stern M E, Pflugfelder S C. Inflammation in dry eye. *Ocul Surf.* 2004; 2:124-130.
2. Pflugfelder S C, de Paiva C S, Li D Q, Stern M E. Epithelial-immune cell interaction in dry eye. *Cornea.* 2008; 27:S9-11.
3. Pflugfelder S C, Stern M E; Symposium participants Immunoregulation on the ocular surface: 2nd Cullen Symposium. *Ocul Surf.* 2009; 7:67-77.
4. Yoon K C, De Paiva C S, Qi H, et al. Expression of Th-1 chemokines and chemokine receptors on the ocular surface of C57BL/6 mice: effects of desiccating stress. *Invest Ophthalmol Vis Sci.* 2007; 48:2561-2569.
5. Yoon K C, Park C S, You I C, et al. Expression of CXCL9. -10, -11, and CXCR3 in the tear film and ocular surface of patients with dry eye syndrome. *Invest Ophthalmol Vis Sci.* 2010; 51:643-650.
6. Arita Y, Kihara S, Ouchi N, et al. Paradoxical decrease of an adipose-specific protein, adiponectin, in obesity. *Biochem Biophys Res Commun.* 1999; 257:79-83.
7. Statnick M A, Beavers L S, Conner L J, et al. Decreased expression of apM1 in omental and subcutaneous adipose tissue of humans with type 2 diabetes. *International Journal of Reproduction and Diabetes Research* 2000; 1: 51-58.
8. Ouchi N, Kihara S, Arita Y, et al. Novel modulator for endothelial adhesion molecules: adipocyte-derived plasma protein adiponectin. *Circulation* 1999; 100: 2473-2476.
9. Matsuda M, Shimomura I, Sata M, Arita Y, Nishida M, Maeda N et al. Role of adiponectin in preventing vascular stenosis. The missing link of adipo-vascular axis. *Journal of Biological Chemistry* 2002; 277: 37487-37491.

10. Wolf A M, Wolf D, Rumpold H, et al. Adiponectin induces the anti-inflammatory cytokines IL-10 and IL-1RA in human leukocytes. *Biochem Biophys Res Commun.* 2004; 323:630-635.
11. Wulster-Radcliffe M C, Ajuwon K M, Wang J, et al. Adiponectin differentially regulates cytokines in porcine macrophages. *Biochem Biophys Res Commun.* 2004; 316: 924-929.
12. Neumeier M, Weigert J, Schäffler A, et al. Different effects of adiponectin isoforms in human monocytic cells. *J Leukoc Biol.* 2006; 79:803-808.
13. Ebina K, Fukuhara A, Ando W, et al. Serum adiponectin concentrations correlate with severity of rheumatoid arthritis evaluated by extent of joint destruction. Clin Rheumatol. 2009; 28:445-451.
14. De Paiva C S, Villarreal A L, Corrales R M, et al. Dry eye-induced conjunctival epithelial squamous metaplasia is modulated by interferon-gamma Invest Ophthalmol Vis Sci. 2007; 48:2552-2560.
15. Díez J J, Iglesias P. The role of the novel adipocyte-derived hormone adiponectin in human disease. Eur. J. Endocrinol. 2003; 148: 293-300.
16. Tang C H, Chiu Y C, Tan T W, et al. Adiponectin enhances IL-6 production in human synovial fibroblast via an AdipoR1 receptor, AMPK, p38, and NF-kappa B pathway. J Immunol. 2007; 179:5483-5492.
17. Stern M E, Gao J, Siemasko K F, et al. The role of the lacrimal functional unit in the pathophysiology of dry eye. Exp Eye Res. 2004; 78:409-416.

What is claimed is:

1. A method for treating a dry eye disease, comprising administering to a subject in need thereof a therapeutically effective amount of a composition comprising an isolated protein comprising the amino acid sequence as set forth in SEQ ID NO:1, as an active ingredient, wherein the administration is performed by a topical administration to ocular surface.

2. The method according to claim 1, wherein the eye disease is a side effect caused by a use of a contact lens.

3. The method according to claim 1, wherein the subject is in need of decreasing a level of inflammatory cytokine before the administration, and the composition decreases the level of inflammatory cytokine.

4. The method according to claim 1, wherein the subject is in need of increasing level of conjunctival goblet cells before the administration, and the composition increases the number of conjunctival goblet cells.

5. The method according to claim 1, wherein the subject is in need of reducing corneal surface irregularity before the administration, and the composition decreases corneal surface irregularity.

6. The method according to claim 1, wherein the composition is a formulation selected from the group consisting of solution, suspension, syrup, emulsion, liposome, dust, powder, granule, tablet, sustained-release, eye drop, capsule, contact lens cleaner and contact lens lubricant.

7. The method according to claim 1, wherein the composition is encapsulated into liposomes.

8. The method according to claim 1, wherein the composition is prepared in a sustained-release formulation.

9. A method for lubricating or moisturizing an eye, comprising applying topically to an eye of a subject in need thereof an artificial tear composition comprising an isolated protein comprising the amino acid sequence as set forth in SEQ ID NO: 1 as an active ingredient.

10. The method according to claim 6, wherein the subject is in need of increasing tear secretion in lacrimal gland, and the active ingredient promotes tear secretion in lacrimal gland.

11. A method for cleaning or lubricating a contact lens, comprising contacting the contact lens with a composition comprising an isolated protein comprising the amino acid sequence as set forth in SEQ ID NO: 1 as an active ingredient.

* * * * *